United States Patent [19]

Maxwell

[11] Patent Number: 5,894,870
[45] Date of Patent: Apr. 20, 1999

[54] SYRINGE GUIDE AND VIAL HOLDER

[75] Inventor: Andrew A. Maxwell, Kalamazoo, Mich.

[73] Assignee: Pharmacia & Upjohn Company, Kalamazoo, Mich.

[21] Appl. No.: 08/872,274

[22] Filed: Jun. 10, 1997

[51] Int. Cl.[6] .................... B65B 1/16; B65B 1/04
[52] U.S. Cl. .................... 141/27; 141/25; 141/26; 141/94; 141/329; 141/330; 604/411; 604/414; 604/415
[58] Field of Search .................... 141/25, 27, 26, 141/94, 95, 329, 330; 604/407, 411, 412, 414, 415

[56] References Cited

U.S. PATENT DOCUMENTS

| | | |
|---|---|---|
| D. 248,314 | 6/1978 | Romero et al. . |
| D. 275,767 | 10/1984 | Capps . |
| D. 280,018 | 8/1985 | Scott . |
| D. 302,726 | 8/1989 | Schwöbel . |
| 1,838,825 | 12/1931 | Goldstein . |
| 2,349,604 | 5/1944 | Barrows . |
| 2,417,902 | 3/1947 | Barrows . |
| 2,586,581 | 2/1952 | Tschischeck . |
| 2,677,372 | 5/1954 | Barnish, Jr. . |
| 3,596,659 | 8/1971 | Glasser . |
| 3,602,272 | 8/1971 | Stawski . |
| 3,610,241 | 10/1971 | LeMarie . |
| 3,610,297 | 10/1971 | Raaf et al. . |
| 3,826,260 | 7/1974 | Killinger . |
| 3,826,261 | 7/1974 | Killinger . |
| 3,833,030 | 9/1974 | Waldbauer, Jr. et al. . |
| 3,840,011 | 10/1974 | Wright . |
| 3,844,318 | 10/1974 | Raia et al. . |
| 3,853,158 | 12/1974 | Whitty . |
| 3,874,380 | 4/1975 | Baum . |
| 3,875,979 | 4/1975 | Hults . |
| 3,976,073 | 8/1976 | Quick et al. . |
| 3,993,063 | 11/1976 | Larrabee . |
| 4,143,428 | 3/1979 | Cohen . |
| 4,178,071 | 12/1979 | Asbell . |
| 4,219,055 | 8/1980 | Wright . |
| 4,252,159 | 2/1981 | Maki . |
| 4,287,988 | 9/1981 | House . |
| 4,434,820 | 3/1984 | Glass . |
| 4,475,915 | 10/1984 | Sloane . |
| 4,489,766 | 12/1984 | Montada . |
| 4,568,346 | 2/1986 | van Dijk . |
| 4,623,344 | 11/1986 | Eriksson . |
| 4,664,259 | 5/1987 | Landis . |
| 4,743,234 | 5/1988 | Leopoldi et al. . |
| 4,768,568 | 9/1988 | Fournier et al. . |
| 4,778,454 | 10/1988 | LaDow . |
| 4,820,277 | 4/1989 | Norelli . |

(List continued on next page.)

FOREIGN PATENT DOCUMENTS

WO 91/00215   1/1991   European Pat. Off. .

OTHER PUBLICATIONS

Exhibit A is a photocopy of the back panel of a package for a Magni–Guide® Insulin Syringe Scale Magnifier and Needle Guide on sale more than one year prior to the filing date of the present application.

Exhibit B is a photocopy of a different package for the Magni–Guide® Scale Magnifier and Needle Guide for Insulin Syringes on sale more than one year prior to the filing date of the present application.

*Primary Examiner*—Robert M. Fetsuga
*Assistant Examiner*—Tuan N. Nguyen
*Attorney, Agent, or Firm*—Van Dyke, Gardner, Linn & Burkhart, LLP

[57] ABSTRACT

A syringe guide and vial holder facilitates the insertion of a syringe into a medicine vial and the subsequent withdrawal of medicine from the vial into the syringe. The syringe guide is constructed of a single piece of material and includes a syringe trough for slidingly supporting the syringe, a vial holder for holding the medicine vial, and a throat therebetween which defines a vial cap slot that limits the movement of the vial. The syringe trough includes a magnifying wall for magnifying the contents of and any indicia on the syringe.

28 Claims, 5 Drawing Sheets

U.S. PATENT DOCUMENTS

| | | |
|---|---|---|
| 4,840,618 | 6/1989 | Marvel . |
| 4,872,494 | 10/1989 | Coccia . |
| 4,986,322 | 1/1991 | Chibret et al. . |
| 5,158,558 | 10/1992 | Melker et al. . |
| 5,240,047 | 8/1993 | Hedges . |
| 5,242,405 | 9/1993 | Howe . |
| 5,247,972 | 9/1993 | Tetreault . |
| 5,279,585 | 1/1994 | Balkwill . |
| 5,279,586 | 1/1994 | Balkwill . |
| 5,292,318 | 3/1994 | Haber et al. . |
| 5,377,725 | 1/1995 | Neff . |
| 5,385,559 | 1/1995 | Mannix . |
| 5,468,233 | 11/1995 | Schraga . |
| 5,487,738 | 1/1996 | Sciulli . |
| 5,498,243 | 3/1996 | Vallelunga et al. . |
| 5,520,659 | 5/1996 | Hedges . |
| 5,542,760 | 8/1996 | Chanoch et al. . |
| 5,554,128 | 9/1996 | Hedges . |

SYRINGE GUIDE AND VIAL HOLDER

BACKGROUND OF THE INVENTION

This invention relates generally to devices for aiding in the self use of syringes, and more particularly, to a guide for inserting a syringe into a vial or medicine bottle.

When using a syringe to inject medicine, it is often desireable to provide a guide or other device to facilitate filling the syringe with the desired medicine from the medicine bottle. The guide helps align the syringe needle with the cap of the medicine vial and provides a more stable connection between the syringe and the medicine vial. While the use of syringe guides has facilitated the use of syringes, especially by non-medical personnel, the prior art syringe guides have left many areas available for improvement.

For example, many prior art syringe guides have failed to include a magnifying lens in the syringe guide to magnify the syringe and the writing on it. The magnifying lens is especially helpful if the syringe guide is intended to be used for injecting medicines customarily used by people with poor or reduced eyesight or in low light environments. The magnification not only helps a user see the writing and numbers on the syringe, and therefore allows the proper volume of medicine to be withdrawn, but it also enhances the visibility of the entire syringe, thus illuminating any undesired air bubbles in the medicine solution.

In addition, the construction of some prior art syringe guides has failed to allow easy extraction of generally all of the medicine in the medicine vial. The amount of medicine which is removed from the vial is determined by the depth of penetration of the needle into the vial. To remove the maximum contents in the vial, the needle should be inserted into the vial no further than the neck of the vial so that when the vial is inverted, as is typically done when filling a syringe, the needle will be immersed in the medicine regardless of the amount of medicine remaining in the vial. This limited penetration depth is especially advantageous given today's high cost of medicine and the consequent desire to avoid waste. While the depth of the needle can always be manually adjusted, a syringe guide which automatically limits the depth of penetration to the desired amount is especially helpful.

Another area for improvement of syringe guides relates to their ease of cleaning. The repeated use of a syringe guide for administering medicine often tends to result in spills of the medicine on the syringe guide. When dry, the spills tend to be opaque and, therefore, are desirably washed off. Some prior art syringe guides, however, are constructed with air pockets in the syringe guide and cannot be immersed in water. If immersed, water droplets and/or condensation remains in the air pockets or spaces preventing proper viewing and use of the syringe on the syringe guide. This non-immersion requirement means that the syringe guide must be carefully washed, which makes the use of the syringe guide more burdensome. Such limited cleaning techniques can also fail to completely clean all medicine residue from the guide, thereby impairing visibility through the guide to the syringe or writing thereon, especially when the guide is designed to enhance visibility of the syringe.

Prior art syringe guides have also suffered from having the medicine vial easily bumped off or out of place with respect to the guide. Such relative insecurity of the medicine vial retention thereby makes the syringe guide more difficult to use, and often necessitates a user having to separately hold the vial using both hands. If the vial must be separately held, the ease of using the syringe is diminished.

It is also desireable that syringe guides be as inexpensive as possible to manufacture, be entirely transparent to enable viewing of the syringe and vial, and be easy to use. The ease of use is increased by both removing any closed apertures on the syringe guide through which the syringe must be carefully threaded and by designing the syringe guide such that the syringe easily slides on it.

A need can therefore be seen for a new syringe guide which overcomes all of these disadvantages of the prior art, and fully takes into account the foregoing design considerations.

SUMMARY OF THE INVENTION

Accordingly, the present invention provides a syringe guide and a vial holder which firmly holds a medicine vial and allows easy sliding movement of a syringe along the guide while limiting insertion of the needle into the vial and enhancing viewing of the syringe and any indicia thereon.

A syringe guide and vial holder according to one aspect of the present invention includes a longitudinally extending syringe trough, a vial support, and a throat. The syringe trough, the vial support, and the throat are constructed in one piece of material with the throat disposed between the syringe trough and the vial support. The syringe trough is adapted to slidingly support a syringe and includes a transparent, magnifying wall which magnifies the syringe and any indicia thereon for easier visibility. The vial support defines a vial cavity which supports at least a portion of the medicine vial and provides resistance to the vial being bumped or knocked off of the syringe guide. The throat defines a retaining structure which is adapted to prevent longitudinal movement of the vial when the vial cap is engaged by the retaining structure.

The syringe guide and vial holder may include a variety of additional features. The syringe guide and vial holder may include a slot defined in the throat which forms the retaining structure. The slot may additionally include a pair of lips allowing the slot to snappingly receive and retain the vial cap in the slot. The syringe trough may include a pair of longitudinally extending edges which support the syringe along a pair of contact lines and thereby enable the syringe to easily slide in the syringe trough. The syringe trough preferably supports the syringe a distance spaced away from the magnifying wall to allow the magnifying wall to magnify the syringe and any indicia thereon, preferably by at least two times. The syringe trough is also preferably dimensioned to prevent the needle on a syringe having a non-disposable needle tip from penetrating further into the vial than the neck of the vial. The limited penetration depth allows easier removal of generally all of the contents of the vial.

A syringe guide and vial holder according to another aspect of the present invention includes a body of unitary construction defining a syringe trough, a vial support, and a throat disposed therebetween. The throat includes a slot which is adapted to snappingly receive the vial cap and retain the vial cap in the slot regardless of the orientation of the syringe guide and vial holder. The syringe guide and vial holder according to this aspect of the invention may also include any of the features discussed above, such as a completely transparent construction, a magnifying wall, support of the syringe on longitudinal edges, etc.

The syringe guide and vial holder of the present invention improves the ease of use of prior known syringe guides and/or vial holders in several respects. The magnifying wall allows the numbers on the syringe and the contents of the syringe, including possible air bubbles, to be more easily seen. The syringe trough provides easy sliding of the syringe on the syringe guide toward and away from the vial. The retaining structure prevents the vial from moving, and therefore frees a user's hand or fingers from having to hold the vial while the syringe needle is inserted therein. The one piece construction of the syringe guide and the vial holder enables it to be economically manufactured and the lack of air pockets allows it to be easily washed by immersion in water or in an automatic dishwasher. The combination of these features provides a novel syringe guide which is both exceptionally easy to use and inexpensive to manufacture.

These and other benefits, results, and objects of the present invention will be apparent to one skilled in the art, in light of the following specification when read in conjunction with the accompanying drawings.

DESCRIPTION OF THE PREFERRED EMBODIMENTS

Figure 1:
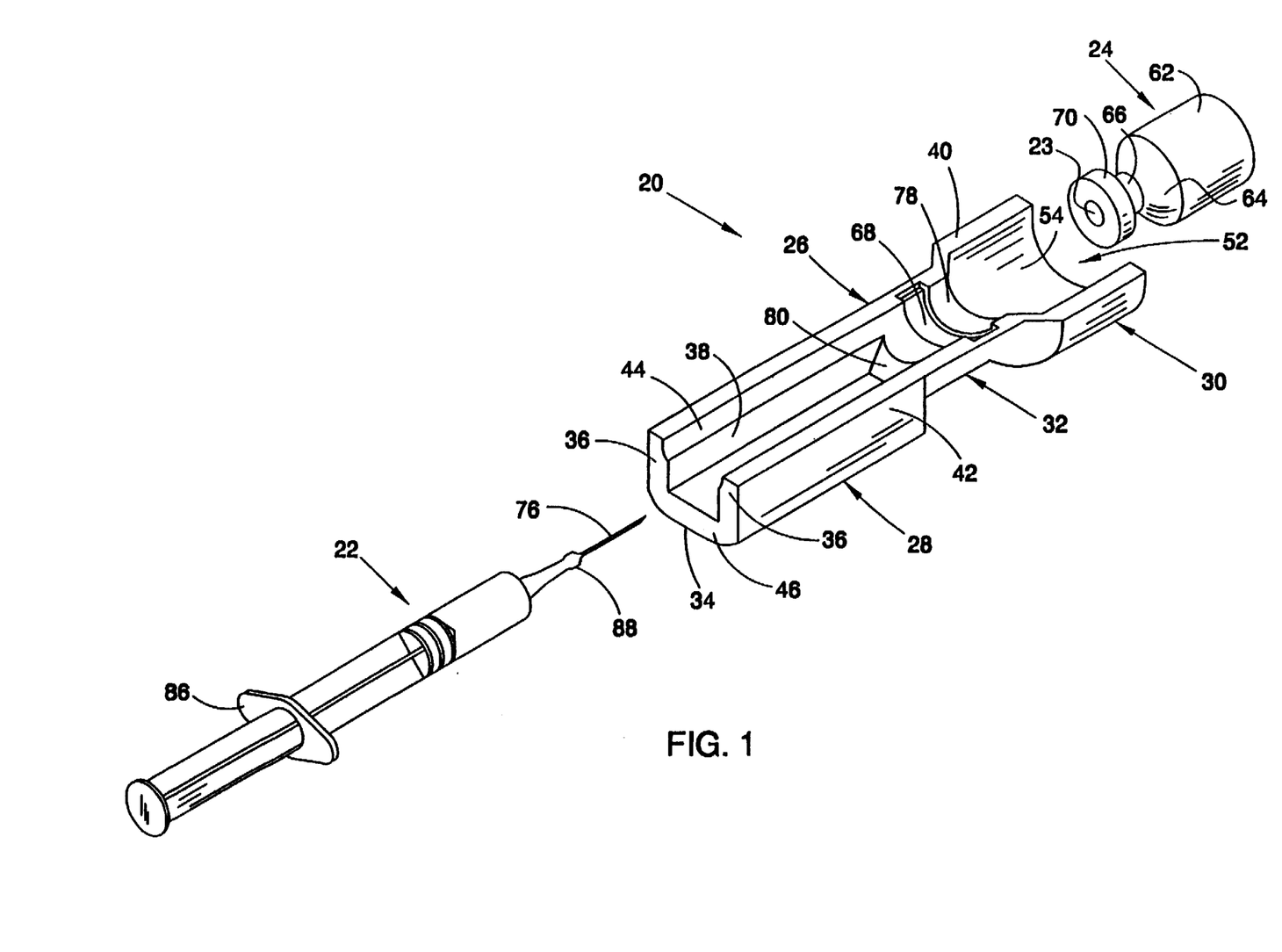
FIG. 1 is a perspective view of a syringe guide and vial holder according to one embodiment of the present invention depicted with a representative syringe and vial.

The present invention will now be described with reference to the accompanying drawings wherein like reference numerals correspond to like elements in the several drawings. A syringe guide and a vial holder 20 according to one embodiment of the present invention is depicted in FIG. 1 between a syringe 22 and a vial 24. Syringe guide and vial holder 20 is designed to receive and secure vial 24 at one end, and to slidingly receive syringe 22 at an opposite end. As shown in FIGS. 1, 9 and 11–12, syringe 22 is slidingly inserted into a penetrable, rubber or other similar section 23 centered in a formed metal cap 70 on the open end of neck 66 of vial 24 and the contents therein is withdrawn. Syringe guide and vial holder 20 is especially designed for use with 1–2.5 ml. syringes, though the dimensions of syringe guide and vial holder 20 can be altered accordingly to accommodate larger or smaller syringes. Syringe guide and vial holder 20 is also especially intended to aid in the self-administration of medicines such as for impotence, though it will be understood that it can be used in a wide variety of other medicinal applications.

Figure 2:
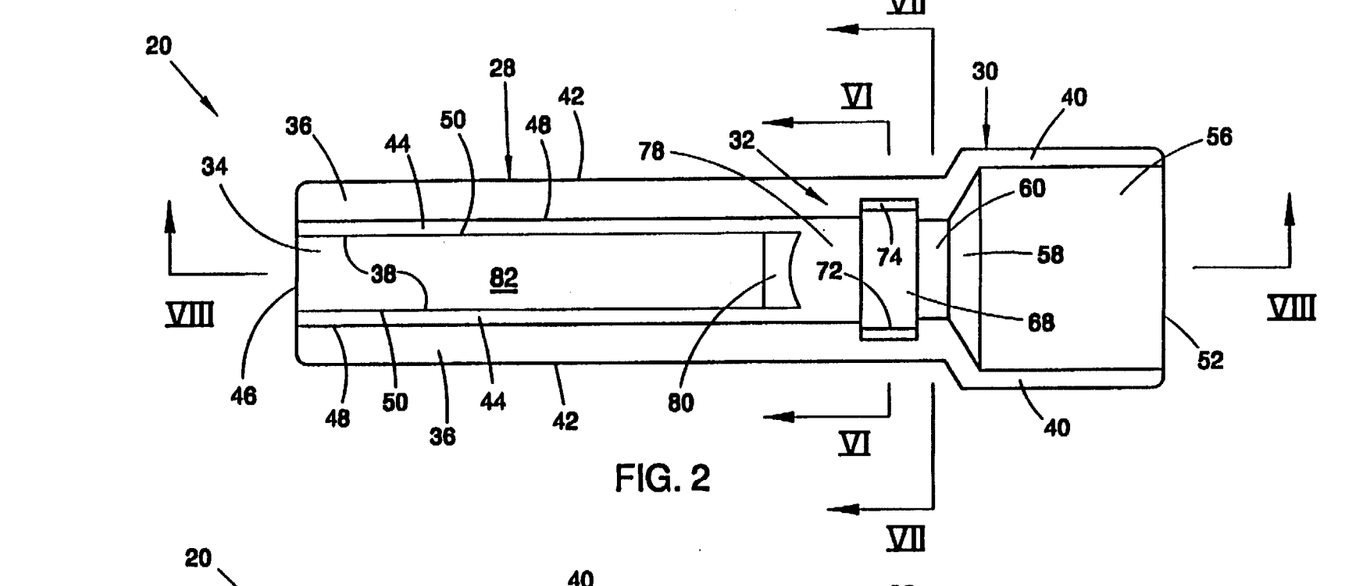
FIG. 2 is a plan view of the syringe guide and vial holder of FIG. 1.
Figure 3:
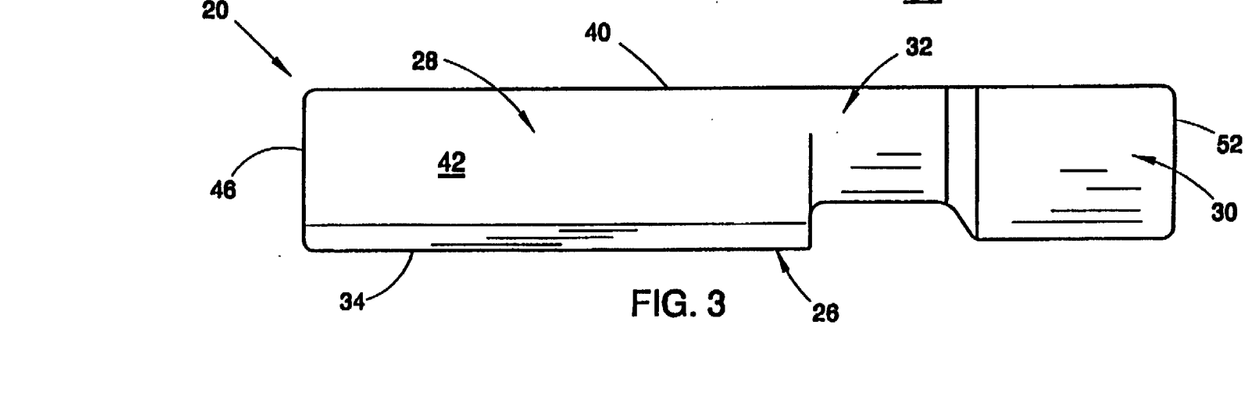
FIG. 3 is a side, elevational view of the syringe guide and vial holder of FIG. 1.
Figures 8, 9, 10:
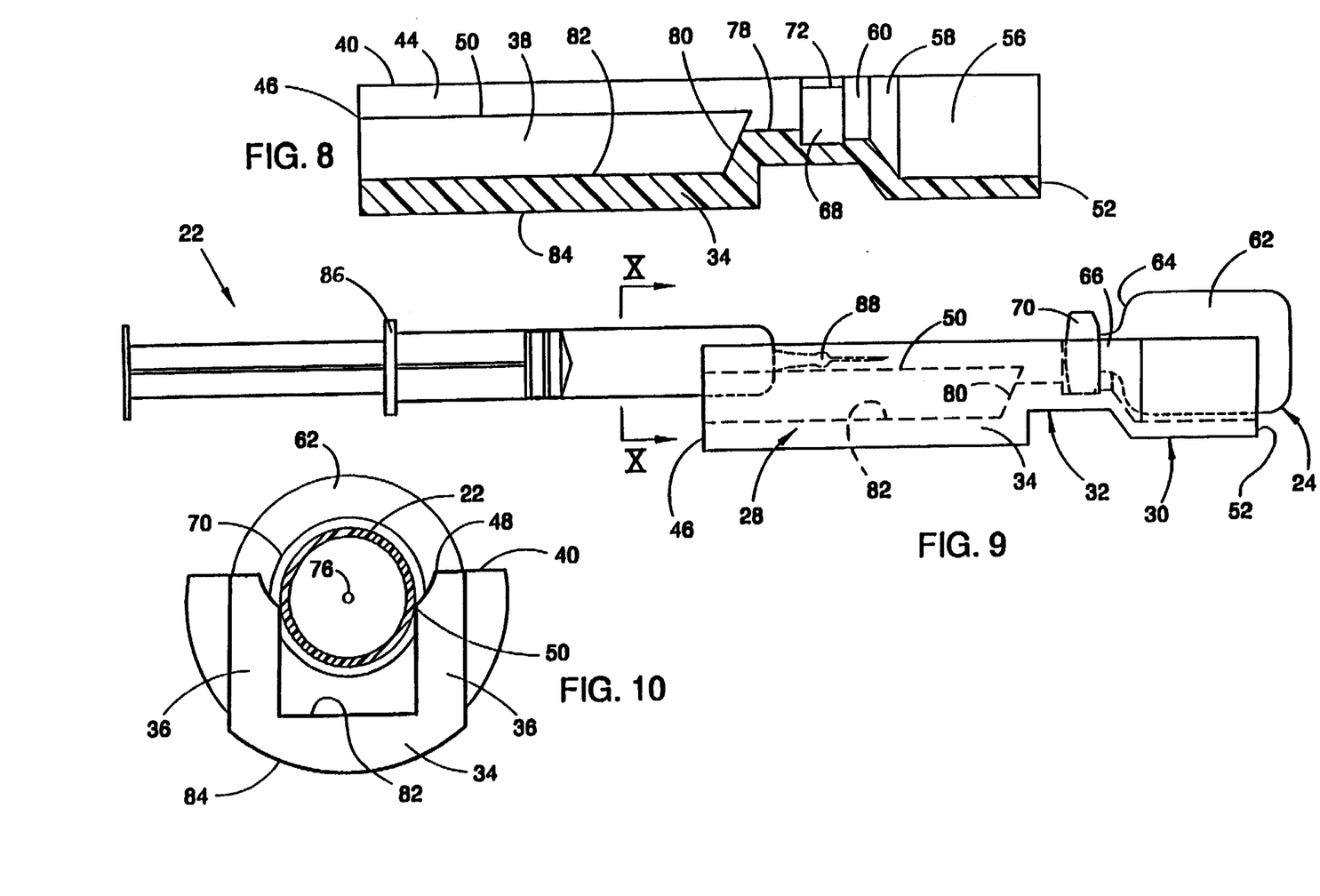
FIG. 8 is a sectional, elevational view of the syringe guide and vial holder of FIG. 2 taken along the line VIII—VIII.
FIG. 9 is a side, elevational view of the syringe guide and vial holder shown supporting a vial and partially supporting a syringe.
FIG. 10 is a sectional, elevational view of the syringe, vial, and syringe guide and show needle 76 in center vial holder of FIG. 9 taken along the line X—X.

Syringe guide and vial holder 20 includes a single-piece body 26 having a syringe trough 28 at one end, a vial holder 30 at an opposite end, and a throat 32 therebetween (FIGS. 1–3). Body 26 is of one-piece, solid construction and includes no air pockets. Body 26 is preferably entirely transparent and can be made such as by injection molding from a wide variety of materials, although a clear, acrylic plastic is preferred. As shown in FIG. 10, syringe trough 28, vial holder 30 and throat 32 are aligned along a common axis in body 26 such that the needle of a syringe placed in syringe trough 28 will pass through throat 32, and be aligned for penetration into penetrable section 23 of the medicine vial.

Longitudinally extending syringe trough 28 includes a magnifying wall 34 and a pair of spaced side walls 36 extending away from magnifying wall 34 at generally right angles (FIGS. 1–4). Side walls 36 each include an interior surface 38 and an exterior surface 42. An arcuate surface 44 is also defined in each side wall 36 between interior surface 38 and a top surface 40 of body 26. Interior surface 38 and arcuate surface 44 extend from a syringe end 46 on syringe guide and vial holder 20 to throat 32. Arcuate surface 44 defines an upper longitudinal edge 48 and a lower longitudinal edge 50. The radius of curvature of arcuate surfaces 44 is slightly greater than the intended radius of curvature of the cylindrical body of syringe 22. As shown in FIG. 10, with these different curvatures, syringe 22 will only contact syringe trough 28 along lower edges 50. The points of contact between syringe 22 and lower edge 50 define a pair of spaced, parallel contact lines. The supporting of syringe 22 by a pair of spaced contact lines defined by lower edges 50, instead of by a surface or pair of surfaces, enables syringe 22 to slide along syringe trough 28 while contacting a smaller surface area. With a smaller surface area, the friction is less, and syringe 22, therefore, more easily slides along syringe trough 28.

Figures 4, 5, 6, 7:
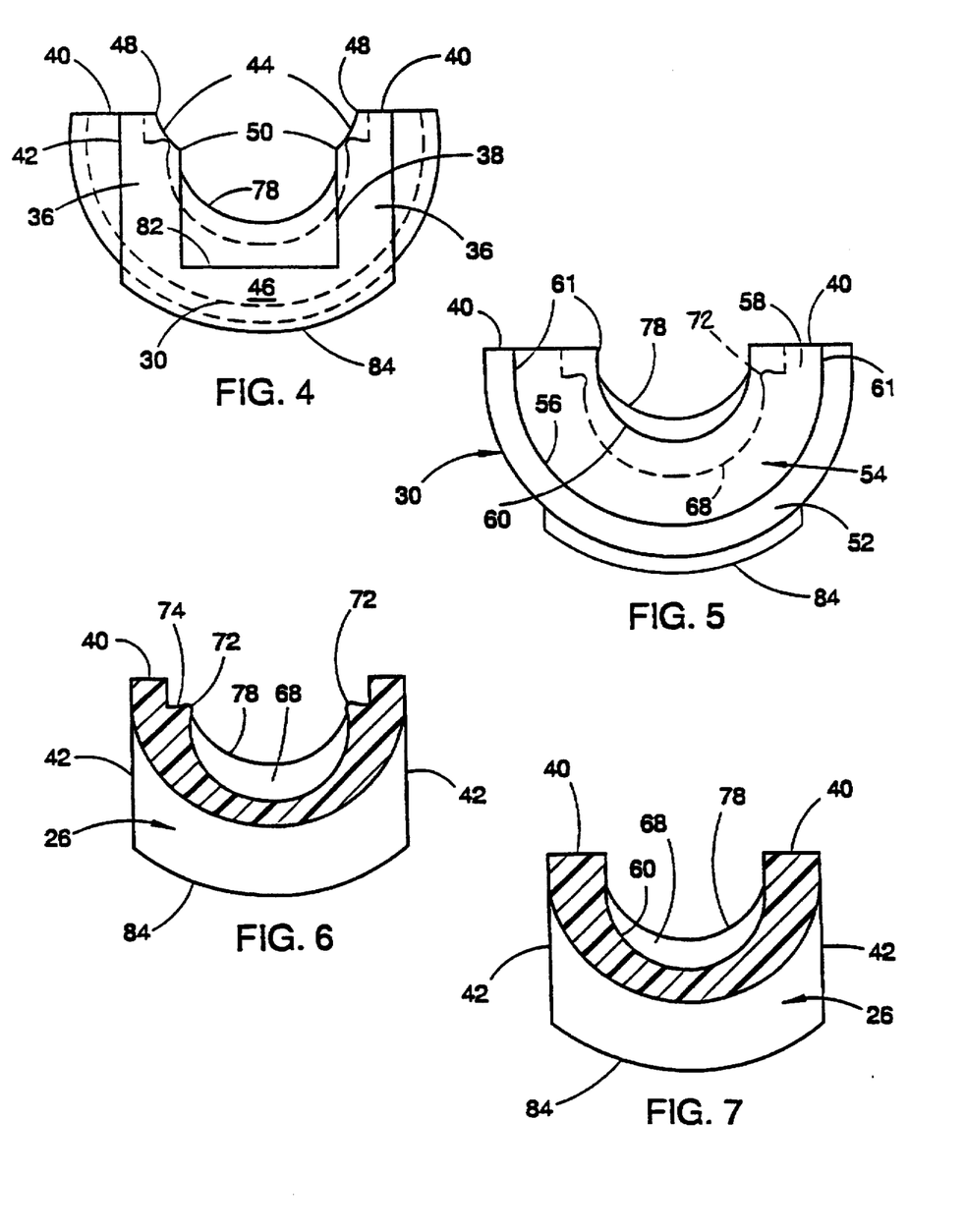
FIG. 4 is an elevational, end view of the syringe trough end of the syringe guide and vial holder of FIG. 1.
FIG. 5 is an elevational, end view of the vial holder end of the syringe guide and vial holder of FIG. 1.
FIG. 6 is a sectional, elevational view of the syringe guide and vial holder of FIG. 2 taken along line VI—VI.
FIG. 7 is a sectional, elevational view of the syringe guide and vial holder of FIG. 2 taken along line VII—VII.

Vial holder 30 is defined in body 26 at a vial end 52 opposite syringe end 46 (FIGS. 1–3 and 5). Vial support or holder 30 includes a vial cavity 54 dimensioned to conform to the shape and contours of a standard medicine vial. In particular, vial cavity 54 includes a generally circular, cylindrical body support surface 56, an angled support surface 58, and a generally circular, cylindrical neck support surface 60. Body support surface 56 is generally configured to support a body 62 of vial 24. Surface 56 has a preferred length which is slightly less than the length of body 62 of vial 24 which enables the end of the vial to be grasped easily when removal is desired while still providing, secure support when vial 24 is mounted therein. Angled support surface 58 conforms generally to a curved top surface 64 on vial 24, and neck support surface 60 generally conforms to and supports a neck 66 on vial 24. Body support surface 56, angled support surface 58, and neck support surface 60 are defined at a depth in body 26 sufficient to surround more than half the circumference of vial 24. Vial 24 is, therefore, firmly fixed and securely held in vial holder 30. To permit vial 24 to be received in vial holder 30 at this depth, body support surface 56, angled support surface 58, and neck support surface 60 are semicircular in cross section at their deepest portion, and each include a straight, vertical surface portion 61 adjacent top surface 40 (FIG. 5).

Throat 32 extends longitudinally between vial holder 30 and syringe trough 28, and defines a vial cap slot 68 (FIGS. 1–3, and 6–8). Vial cap slot 68 is generally semi-circular and of a radius sightly greater than the radius of annular cap 70 on vial 24 to permit cap 70 to fit therein. Because of the larger diameter of cap 70 on vial 24, slot 68 is deeper than neck support surface 60 (FIGS. 5 and 8). Vial cap slot 68 includes a pair of lips 72 defined on opposite sides of vial cap slot 68 adjacent a recessed top surface 74 (FIG. 6). Lips 72 extend inwardly and define a distance therebetween which is slightly smaller than the outside diameter of vial cap 70. Recessed top surface 74 is generally parallel to top surface 40, but indented into body 26 a small distance. By defining lips 72 adjacent recessed top surface 74, the slight vertical extension of lips 72 will not extend beyond top surface 40, and top surface 40 can therefore be entirely flat. The sides of slot 68 including lips 72 are resiliently flexible and permit cap 70 of vial 24 to be snapped past lips 72 and into vial cap slot 68. When snapped in this fashion, vial 24 will remain in vial cavity 54 regardless of the orientation of syringe guide and vial holder 20. In other words, it requires more force than the weight of vial 24 to remove vial 24 from its snapping engagement in vial cap slot 68. The force required to snap vial 24 out of vial cap slot 68, however, is not so great that it cannot be easily produced by users of all strengths and dexterities. The snapping engagement and consequent retention of vial 24 into vial cap slot 68 provides a free hand for a user of syringe guide and vial holder 20 which would otherwise be required to hold vial 24 in place. This enables easier manipulation and use of a syringe in syringe guide and vial holder 20. The depth of vial cap slot 68 in body 26 is such that a needle 76 on syringe 22 which is resting in syringe trough 28 will penetrate the rubber portion 23 of cap 70 of vial 24 generally in its center (see FIG. 10).

Figure 11:
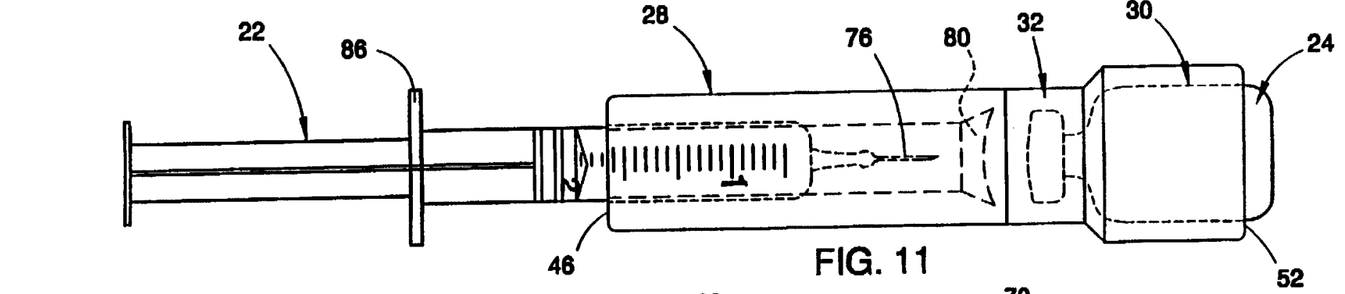
FIG. 11 is a bottom view of the syringe, the vial, and the syringe guide and vial holder illustrating the magnification provided by the syringe guide and vial holder.

A cylindrical throat surface 78 extends from vial cap slot 68 to an angled trough surface 80 (FIG. 9). Angled trough surface 80 slopes downwardly to a generally flat, top or inner surface 82 of magnifying wall 34. Surface 82 of magnifying wall 34 extends longitudinally from angled trough surface 80 to syringe end 46. As can be seen in FIGS. 9, 10, 12, and 13, syringe trough 28 supports syringe 22 a spaced distance above top surface 82 of magnifying wall 34. This spaced distance provides a focal distance for the magnification of syringe 22 by magnifying wall 34. Magnifying wall 34 includes a bottom arcuate surface 84 which acts like a lens for the magnification provided by magnifying wall 34. The focal distance of the syringe and the curvature of bottom arcuate surface 84 may be altered to provide different degrees of magnification of syringe 22, through a magnification of 2–3 times is preferred. The magnification of syringe 22 is visible when viewed through magnifying wall 34 from below as shown in FIG. 11.

Figure 12:
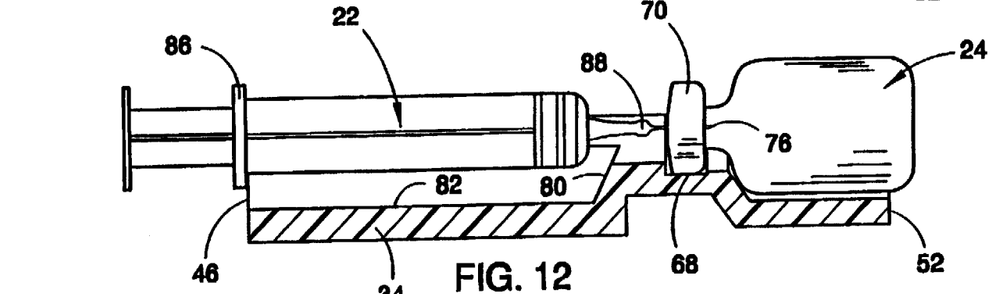
FIG. 12 is a sectional view of the syringe guide and the vial holder illustrating the preferred type of syringe with a permanent, non-disposable needle inserted into the vial.

To use syringe guide and vial holder 20, syringe 22 is placed in syringe trough 28 such that it rests against, and is supported by lower edges 50 of side walls 36. Vial 24 is positioned in vial cavity 54 and cap 70 of vial 24 is snapped past lips 72 into vial cap slot 68. Syringe 22 is then slid toward vial 24 in syringe trough 28 on edges 50 until needle 76 of syringe 22 penetrates cap 70 of vial 24. When syringe 22 includes an integrally attached, permanent, non-disposable needle 76 instead of a separately disposable needle tip 90 (FIG. 13), the sliding movement of syringe 22 towards vial 24 will terminate when finger flanges 86 abut against syringe end 46 of syringe guide 20. When syringe guide and vial holder 20 is used with these syringes having non-disposable needle tips, a hub 88 on syringe 22 remains spaced from cap 70 of vial 24 because of the contact of finger flanges 86 against syringe end 46 (FIG. 12). The spacing of hub 88 of syringe 22 from cap 70 of vial 24 ensures that needle 76 does not penetrate further into vial 24 than the neck 66 of vial 24. This limited penetration ensures that, when vial 24 is held up side down, syringe 22 can remove substantially all of the medicine contained in vial 24, thereby reducing any waste of the medicine.

Figure 13:
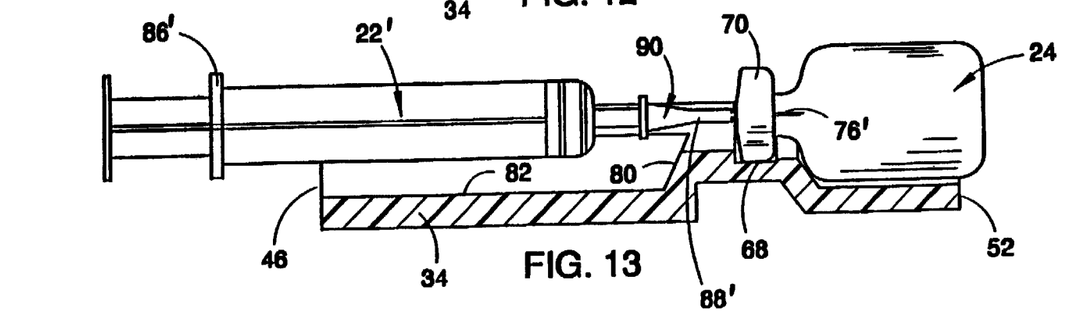
FIG. 13 is a side, sectional view of the syringe guide and vial holder illustrating a second type of syringe having a removable, disposable needle inserted into the vial.

If syringe guide and vial holder 20 is used with a syringe 22' which includes a disposable needle tip 90 having needle 76', then syringe 22' can be slid towards vial 24 until hub 88' contacts cap 70 of vial 24 (FIG. 13). The combined length of syringe 22' with disposable needle tip 90 is longer than that of syringe 22 with non-disposable hub 88 and needle 76. In such a case, needle 76' will penetrate into vial 24 a slightly greater distance, although nearly all of the contents of vial 24 can still be easily extracted via syringe 22.

Regardless of which syringe 22 or 22' is used with syringe guide and vial holder 20, angled trough surface 80 remains spaced from and out of any contact with any part of the syringe. Any limitation on sliding movement of the syringe in trough 28 is provided by end surface 46 acting against finger flanges 86, or by needle tip 90 acting against penetrable section 23 of vial cap 70.

It will also be apparent that the preferred solid, one-piece construction of syringe guide and vial holder 20 from molded plastic such as acrylic enables easy cleaning simply by hand washing the entire guide by immersing it in water and gently washing with a mild, non-abrasive detergent, or by washing the guide in a conventional automatic dishwashing machine. In either case, no water, liquid, fog, steam or condensation will remain on any surface, all of which are easily accessible to be wiped clean and dried. Thus no condensation collects on any part, especially the surfaces of a magnifying wall 34, which condensation could otherwise impair visibility through and magnification by wall 34.

While the present invention has been described in terms of the preferred embodiments discussed in the above specification, it will be understood by one skilled in the art that the present invention is not limited to these particular preferred embodiments, but includes any and all such modifications that are within the spirit and scope of the present invention as defined in the appended claims.

The embodiments of the present invention in which an exclusive property or privilege is claimed are defined as follows:

1. A syringe guide and vial holder, comprising:
    a longitudinally extending syringe trough adapted to support a syringe, said syringe trough including a transparent, magnifying wall which magnifies the syringe and any indicia thereon;
    a vial support defining a vial cavity dimensioned to support at least a portion of the vial;
    a throat disposed between said syringe trough and said vial support, said throat defining a retaining structure which includes a pair of lips that snappingly receive a cap on the vial, said retaining structure adapted to prevent longitudinal movement of the vial both toward and away from said syringe trough when the cap on the vial engages said retaining structure; and
    said syringe trough, said vial support, and said throat being of one-piece construction.

2. The syringe guide and vial holder of claim 1 wherein said retaining structure is a slot defined in said throat and said slot is adapted to receive the cap on the vial.

3. A syringe guide and vial holder, comprising:

a longitudinally extending syringe trough adapted to support a syringe, said syringe trough including a transparent, magnifying wall which magnifies the syringe and any indicia thereon;

a vial support defining a vial cavity dimensioned to support at least a portion of the vial;

a throat disposed between said syringe trough and said vial support, said throat defining a slot which is adapted to receive a cap on the vial and prevent longitudinal movement of the vial when the cap on the vial engages said slot;

said slot including a pair of lips which are adapted to snappingly retain the cap of the vial in said slot such that the vial will remain in said vial cavity when the cap is snapped in said slot regardless of the orientation of said syringe guide and vial holder; and said syringe trough, said vial support, and said throat being of one-piece construction.

4. The syringe guide and vial holder of claim 3 wherein said vial cavity envelopes more than half of the circumference of the vial.

5. The syringe guide and vial holder of claim 1 wherein said syringe trough includes a pair of spaced, longitudinal side walls extending away from said magnifying wall, said side walls supporting said syringe at a distance spaced away from said magnifying wall.

6. The syringe guide and vial holder of claim 5 wherein said distance is sufficient to enable said magnifying wall to magnify said syringe at least twice.

7. The syringe guide and vial holder of claim 5 wherein each of said spaced, longitudinal side walls defines at least one longitudinal edge, said side walls being dimensioned to support the syringe on said longitudinal edges along the entire length of said syringe trough.

8. The syringe guide and vial holder of claim 1 wherein said syringe guide and vial holder is constructed entirely of transparent material.

9. The syringe guide and vial holder of claim 8 wherein said syringe guide and vial holder is molded from clear acrylic material.

10. The syringe guide and vial holder of claim 1 wherein said syringe trough is dimensioned to prevent a non-disposable needle tip on a syringe from penetrating further into the vial than a neck of the vial.

11. The syringe guide and vial holder of claim 10 wherein said trough has an end surface adapted to engage finger flanges on the syringe when fitted therein, said trough having a length from said end surface to said throat adapted to allow the syringe needle tip to penetrate only into the neck of the vial.

12. The syringe guide and vial holder of claim 1 wherein said vial cavity supports a majority of the length of the vial.

13. A syringe guide and vial holder, comprising:

a body of unitary construction defining a longitudinally extending syringe trough, a vial support, and a throat disposed therebetween;

said longitudinally extending syringe trough including a transparent magnifying wall which magnifies the size of the syringe and any indicia thereon when the syringe is viewed through said magnifying wall;

said vial support dimensioned to support a majority of the length of the vial; and said throat defining a slot which includes a pair of lips adapted to snappingly receive a cap on the vial, said slot adapted to prevent longitudinal movement of the vial both toward and away from said syringe trough when the vial cap is placed in said slot.

14. A syringe guide and vial holder, comprising:

a body of unitary construction defining a longitudinally extending syringe trough, a vial support, and a throat disposed therebetween;

said longitudinally extending syringe trough including a transparent magnifying wall which magnifies the size of the syringe and any indicia thereon when the syringe is viewed through said magnifying wall;

said vial support defining a vial cavity dimensioned to support a majority of the length of the vial; and said throat defining a slot adapted to receive a cap on the vial and to prevent longitudinal movement of the vial when the vial cap is placed in said slot, said slot including a pair of lips which are adapted to snappingly retain the cap of the vial in said slot such that the vial will remain in said vial cavity when the cap is snapped in said slot regardless of the orientation of said syringe guide and vial holder.

15. The syringe guide and vial holder of claim 14 wherein said vial cavity envelopes more than half of the circumference of the vial.

16. The syringe guide and vial holder of claim 13 wherein said syringe trough includes a pair of spaced, longitudinal side walls extending away from said magnifying wall, said side walls supporting said syringe at a distance spaced away from said magnifying wall.

17. The syringe guide and vial holder of claim 16 wherein said distance is sufficient to enable said magnifying wall to magnify said syringe at least twice.

18. The syringe guide and vial holder of claim 16 wherein each of said spaced, longitudinal side walls defines a longitudinal edge, said side walls being dimensioned to support the syringe on said longitudinal edges along the entire length of said syringe trough.

19. The syringe guide and vial holder of claim 13 wherein said syringe guide and vial holder is constructed entirely of transparent material.

20. The syringe guide and vial holder of claim 19 wherein said syringe trough is dimensioned to prevent a non-disposable needle tip on a syringe from penetrating further into the vial than the neck of the vial.

21. The syringe guide and vial holder of claim 19 wherein said trough has an end surface adapted to engage finger flanges on syringe when fitted therein, said trough having a length from said end surface to said throat adapted to allow the syringe needle tip to penetrate only into the neck of the vial.

22. A syringe guide and vial holder, comprising:

a body of unitary construction defining a longitudinally extending syringe trough, a vial support, and a throat disposed therebetween;

said longitudinally extending syringe trough including a transparent magnifying wall and a pair of spaced side walls extending away from said magnifying wall, said side walls adapted to support the syringe a spaced distance away from said magnifying wall, and said magnifying wall adapted to magnify the size of the syringe and any indicia thereon when the syringe is viewed through said magnifying wall;

said vial support defining a vial cavity dimensioned to receive and support a majority of the length of the vial; and said throat defining a slot adapted to receive a cap on the vial, said slot including a pair of spaced lips which prevent removal of said cap from said slot without flexing said lips.

23. The syringe guide and vial holder of claim 22 wherein each of said spaced, longitudinal side walls defines at least one longitudinal edge, said side walls being dimensioned to support the syringe on said longitudinal edges along the entire length of said syringe trough.

24. The syringe guide and vial holder of claim 23 wherein said syringe guide and vial holder is constructed entirely of transparent material.

25. The syringe guide and vial holder of claim 24 wherein said syringe trough is dimensioned to prevent a non-disposable needle tip on a syringe from penetrating further into the vial than the neck of the vial.

26. A syringe guide and vial holder, comprising:
- a body of unitary construction defining a longitudinally extending syringe trough, a vial support, and a throat disposed therebetween;
- said longitudinally extending syringe trough adapted to support a syringe;
- said vial support adapted to support at least a portion of the length of the vial; and
- said throat defining a slot including a pair of lips adapted to snappingly receive a cap on the vial and retain the cap in said slot regardless of the orientation of said syringe guide and vial holder.

27. The syringe guide and vial holder of claim 26 wherein said syringe trough has spaced edges defining elongated contact lines for supporting the barrel of a syringe for ease of sliding movement.

28. The syringe guide and vial holder of claim 27 wherein said syringe guide and vial holder is constructed entirely of transparent material.

* * * * *